United States Patent [19]

Kaye

[11] Patent Number: 5,128,549
[45] Date of Patent: Jul. 7, 1992

[54] STRAY RADIATION COMPENSATION

[75] Inventor: Wilbur I. Kaye, Corona Del Mar, Calif.

[73] Assignee: Beckman Instruments, Inc., Fullerton, Calif.

[21] Appl. No.: 502,359

[22] Filed: Mar. 30, 1990

[51] Int. Cl.$^5$ ................................................ G01J 3/36
[52] U.S. Cl. ........................................ 250/372; 356/307; 356/328
[58] Field of Search ............... 356/300, 328, 326, 319, 356/307, 308; 250/372

[56] References Cited

U.S. PATENT DOCUMENTS

| | | | |
|---|---|---|---|
| 3,937,965 | 2/1976 | Vasseur | 378/7 |
| 4,526,470 | 7/1985 | Kaye | 356/319 |
| 4,616,210 | 10/1986 | Ferber et al. | 356/319 |
| 4,687,329 | 8/1987 | Schultz | 356/328 |
| 4,715,712 | 12/1987 | Nogami | 356/308 |
| 4,798,464 | 1/1989 | Boostrom | 356/328 |
| 4,820,048 | 11/1989 | Barnard | 356/328 |
| 4,875,773 | 10/1989 | Burns et al. | 356/328 |

FOREIGN PATENT DOCUMENTS

| | | | |
|---|---|---|---|
| 0167750 | 1/1986 | European Pat. Off. | |
| 178227 | 10/1983 | Japan | 356/300 |
| 2217445 | 10/1989 | United Kingdom | 356/307 |

OTHER PUBLICATIONS

Kaye, Wilbur I.; "Stray Radiation"; *Advances in Standards and Methodology in Spectrophotometry* (Analytical Spectroscopy Library; vol. 2) Series, (1987) pp. 257-275.

Kaye, Wilbur; "Stray Light Ratio Measurements"; *Anal. Chem.* (1981) vol. 53, pp. 2201-2206.

Kaye, Wilbur; "Stray Radiation from Ruled Gratings"; *Anal. Chem.* (1983) vol. 55, pp. 2022-2035.

Talmi, Yair; "Spectrophotometry and Spectrofluorometry with the Self-scanned Photodiode Array"; *Applied Spectroscopy* (1982) vol. 36, No. 1, pp. 1-18.

*Primary Examiner*—Carolyn E. Fields
*Attorney, Agent, or Firm*—William H. May; P. R. Harder; Wen Liu

[57] ABSTRACT

A method of measuring and compensating stray light in absorbance analysis that use a multiple element array detector wherein one or more of the elements of the diode array are utilized to detect stray radiation in the absence of primary radiation including higher order diffracted radiation. In one aspect, the atmosphere is used to filter all primary radiation below a particular wavelength so that one or more array elements corresponding to detection below such wavelength can be dedicated to the detection of only stray radiation. Detection of higher order diffractions can be prevented by dividing the total spectrum into intervals and detecting these intervals in sequence. In another aspect, a diode array is designed to include additional elements along one side of the array outside the exposure of the primary radiation for the sole purpose of detecting stray radiation.

6 Claims, 2 Drawing Sheets

STRAY RADIATION COMPENSATION

BACKGROUND OF THE INVENTION

1. Field of the Invention

The present invention relates generally to the field of spectrophotometry and more particularly to the compensation of sample measurements for stray light.

2. Description of Related Art

Spectrophotometers can be described as instruments that measure the relative amount of radiant energy absorbed or transmitted by a sample for one or more radiation wavelengths. Such instruments generally include a continuum radiation source, i.e., one which generates radiant energy over a relatively broad band of wavelengths. For a so called "scanning" spectrophotometer, a schematic diagram of typical of the prior art is shown in FIG. 1, monochromator 10 receives the radiation 13 from the source 12 and isolates an output beam 14 comprising radiation having wavelengths substantially within a relatively narrow wavelength band. In the particular example shown, the monochromator 10 includes an entrance slit 16 which receives the radiation of the source 12 through a focusing lens 17, a collimating lens relaying parallel radiation onto a rotatable disperser 20 which breaks up the radiation into its wavelength components spatially, and a second collimating lens 22 which focuses the radiation onto an exit slit 24. Depending on the tilt of the disperser 20 and/or the opening in the exit slit 24, a particular band of radiation can be selectively output by the monochromator 10.

The monochromator output beam 14 is directed to a detector 26 which produces an electrical output having a value related primarily to the radiant power received by the detector and the spectral sensitivity of the detector. In the absence of any radiation falling on the detector, a relatively small signal called the "dark current" may arise from either the detector or the associated electronics. This "dark current" is easily determined by blocking the beam and measuring the output signal. The difference between the total signal and the dark current is called "detected radiant power" (DRP) and is the portion of the detector output generated only in response to incident radiant power.

The beam path 14 between the monochromator 10 and the detector 26 is accessible to the user of the instrument so that sample or reference materials can be place into the beam in a cell 28. Usually, the relative transmittance or absorbance of a sample with respect to a reference material is measured. For example, for given radiation wavelengths within the narrow wavelength band, the reference material is placed into the beam 14 between the monochromator 10 and the detector 26 and the resulting DRP is measured. The reference material is removed and, with the sample in its place, a second DRP is measured. The sample transmittance is then expressed as a ratio of the second (sample) DRP with respect to the first (reference) DRP. Absorbance is related to transmittance by the conversion expression A = —log T, where A is absorbance and T is transmittance. It will be recognized that although various examples and discussions included herein are presented in terms of transmittance, such examples and discussions are equally applicable to the measurement of absorbance since absorbance and transmittance are related terms for the same phenomenon.

Referring to FIG. 2, the monochromator wavelength band may be largely defined by two parameters, half band width 32 and central wavelength 34. The half bandwidth 32 is generally defined as the wavelength interval at which the DRP of the narrow wavelength band 31 is one-half the maximum DRP in the band. The half bandwidth 32 is usually dependent upon the width of monochromator entrance and exit slits 16 and 24 through which the continuum radiation 13 and the output beam 14 pass, respectively. The central wavelength 34 is the wavelength corresponding to the maximum DRP. Ideally the DRP should fall to zero at wavelengths equal to the central wavelength 34 plus and minus a half band width value, i.e. at the points indicated by 37. In practice this is never the case. Two factors complicate this ideal situation. The shape of the DRP versus wavelength graph, (FIG. 2), called the "slit function", may not be triangular and a small DRP may arise from radiation of wavelengths at 39 far removed from the central wavelength 34 as will be explained below.

In some types of spectrophotometers the central wavelength 34 is determined by means of a mechanism that rotates the disperser 20 within the monochromator. This mechanism may incorporate a dial or digital readout intended to display the central wavelength corresponding to the maximum DRP. It is important to recognize that this dial reading does not necessarily correspond to the actual central wavelength of maximum DRP. The difference between the dial reading of wavelength and the actual central wavelength of maximum DRP is usually called the wavelength error. While effort is made to minimize this wavelength error, it may become significant, particularly near the extremes of disperser rotation. In this discussion a distinction will be made between the dial reading of wavelength and the actual central wavelength.

Ideally, the monochromator 10 should pass only radiation having wavelength within the narrow wavelength band, that is, the monochromator output beam 14 should be free of radiation with wavelength outside of an interval 37 twice the width of the half bandwidth 34 and centered at the dial setting wavelength 36. However, such ideal monochromators do not exist. In addition to radiation with wavelength within such an interval 37, which has been called "primary radiation", the monochromator output also includes radiation at wavelengths 39 outside the interval of primary radiation. Such radiation has been referred to in the art as "stray light" and is often a result of light scattering by the disperser 20 within the monochromator 10. The ratio of detected stray radiation to the total detected radiation is known as stray radiant power ratio (SRPR).

The spectral and spatial character of the primary radiation follows the laws of diffraction, i.e. specific portions of the beam are directed to the exit slit or to an equivalent array detector element. On the other hand, the stray radiation is broadly scattered everywhere within the monochromator. The direction of scatter is little affected by the spectral character of the radiation passing the entrance slit. It is not intended to say that the scattered rays uniformly illuminate the inside of the monochromator. Rather the area near the inside of the exit slit (or the detector array in a diode array instrument) is illuminated by stray (white) light much like the space in front of an automobile headlight. Intensity of radiation decreases as the angle between the scattered and diffracted rays increases.

While "stray light" is used herein as just described for the purpose of discussion of the prior art, it will be recognized by those skilled in the art that the term "stray light" has not been clearly defined or limited in use in the prior art. The term has been used variously to denote the overall problem of stray light in spectrophotometers, or a measured quantity of stray light, usually unknown units, or dimensionless ratio such as SRPR. It will also be noted that "light" is synonymous with "radiation" and that "radiation" as used herein includes electromagnetic radiation throughout the ultraviolet, visible and infrared wavelength regions.

Stray light is usually of interest in two contexts. First, it is a general practice of spectrophotometer instrument manufacturers to measure stray light for a particular spectrophotometer and to publish the measurement as an instrument performance specification. Periodically, a spectrophotometer should be retested to determine whether the spectrophotometer till meets the specification. A failure of the instrument to do so is an indication that the spectrophotometer performance may have degraded and that service may be required.

A second context is the measurement of sample transmittance where it is desirable to compensate for the effects of stray light. In the past, stray light induced error has been reduced by limiting the wavelength interval of detectable radiation by means of blocking filters and choice of sources. The blocking filter 30 is positioned between the sample cell 28 and the detector 26. The filter should be highly transmitting to the desired radiation wavelength yet absorb much of the stray radiation. Typically, the bandwidth of a blocking filter is much wider than the half bandwidth or resolution of the monochromator so that one blocking filter may cover an interval of many half bandwidths. Referring to FIG. 2 the dotted lines 38 in the figure are representative of the distribution of detected radiation in the presence of a blocking filter. This method reduces both scattered and multiple order diffracted radiation. However, the blocking filter alone does not, usually, reduce the stray light error as much as is desired and both blocking filter and compensation methods are employed simultaneously.

U S. Pat. No. 4,526,470 issued to the same inventor and assigned to the same assignee as the present invention and the article "Stray Radiation" by the inventor published in *Advances in Standards and Methodology in Spectrophotometry*, Elsevier Science publishers (1987), pages 257-275, describe different approaches of measuring and compensating for stray light. While these methods have been successful in compensating stray light in conventional scanning spectrophotometers, i.e. one which utilizes a monochromator to isolate an output beam of radiation within a relatively narrow wavelength band, compensation of stray light is inherently more difficult in diode-array instrumentation.

In a diode-array spectrophotometer, the broad band of radiant energy of the radiation source is directed through the sample, with the transmitted radiation dispersed into a spectrum by a grating before being directed to an array of photodiodes, i.e. the transmitted radiation is broken up spatially into its wavelength components which are diffracted by an amount according to the wavelength values. Each diode in the array is exposed to a small wavelength interval of the entire spectrum. The perceived wavelength is dependent on the location of the respective diode. Each diode element detects the transmitted radiant intensity of a small wavelength interval to provide an indication of the absorbance of the sample component at the respective wavelength as identified based on the location of the diode element. The overall bandwidth and the spatial resolution of the diode array will depend on the number and size of each discrete element, their spacing, and other optical parameters of the instrument. In order to obtain a broad bandwidth as well as a high resolution, a large number of small diode elements at close spacing are required.

It is difficult to compensate for stray light in a diode array spectrophotometer. As will be described more fully hereinbelow in the detailed description of the present invention, the most important and desirable feature of the diode array instrument is the array. It allows the simultaneous measurement of a broad spectrum of the light source and it has no moving element. However, the desire to process the detected radiation at all wavelength simultaneously frustrates the use of blocking filters to reduce stray light. Since the sample is placed further upstream in the optical path (upstream of the disperser) as compared to conventional scanning spectrophotometers (sample placed downstream of the disperser), this makes the measurement of sample transmittance with respect to wavelengths sensitive to the refractive index and optical path of the sample. It is difficult to insert a blocking filter into the optical configuration without risking abridging the spectral interval. Blocking filters have to be located immediately in front of the detector elements and must be very thin to avoid defocusing or shadowing of adjacent elements. The extremely small size and separation of detector elements exacerbates this problem.

When one uses a diode array, ideally one would like detectable radiation falling on each element in the absence of the sample to be constant and independent of wavelength throughout the range of the instrument. In some instruments, this is partially accomplished by tailoring the length of the diode elements. While this facilitates signal processing it does not reduce the stray light component.

Furthermore, stray light from second and higher order diffractions at the grating can be particularly troublesome. This can be so bad as to force use of one or more blocking filters in spite of the difficulty. One prior method involves limiting spectral intervals to less than one grating order and changing the blocking filter for each order. This partially defeats the goal of a fast scan and still leaves a high stray light unless compensation for stray light is also employed.

SUMMARY OF THE INVENTION

The present invention is directed to a method of measuring and compensating stray radiation in spectrophotometers which use diode arrays as detectors. One or more of the array elements are used to detect only stray radiation and the measurement is subtracted from the total transmittance.

In one aspect of the invention, an array element is chosen at a location where it will not be subjected to primary radiation. This element is dedicated for stray radiation detection. The corresponding wavelength of the array element is conveniently chosen to be within the wavelength range in which all primary radiations are absorbed by the air in the instrument. To avoid any effect of higher order diffractions of shorter wavelength on the primary radiation measurements at higher wavelengths, blocking filters are employed to block out the shorter wavelength higher order radiations when higher wavelength radiations are measured. The stray radiation measuring array element can be chosen to be one just below the filter cut off wavelength.

In another aspect of the invention, a moving optical element is provided to direct the radiation transmitted through the sample to a number of slits in sequence prior to dispersion, so as to break up the spectrum into several wavelength intervals to avoid the effects of higher order diffractions. A single diode array can be used full scale to detect each range of wavelength in sequence by using an appropriate dispersion grating.

In a further aspect of the invention, a novel diode array design is proposed which is especially suited for stray radiation measurement and compensation. The diode array has one or more additional elements arranged along a longitudinal edge of the conventional diode array outside the coverage of the primary radiation. These additional elements are dedicated for stray radiation detection. The diode array can be divided into sectors of wavelength ranges each including an associated stray radiation element and appropriate blocking filters are coated on each sector to block second and higher order diffractions. Since the additional array element associated with the respective sector is covered by the same filter which covers the primary radiation detector elements in the same sector, optical disparity between the elements in the same sector can be avoided.

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

Figure 3:
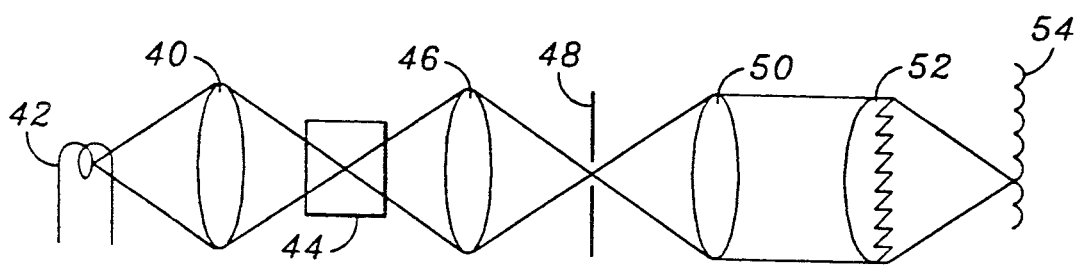
FIG. 3 is a schematic diagram of a diode array spectrophotometer.

FIG. 3 shows a schematic of a diode array spectrophotometer. A relay lens 40 focuses the radiation from the source 42 to a sample cell 44. Another lens 46 images the transmitted radiation onto an entrance slit 48. A lens 50 collimates the radiation from the slit 48 into a beam directed at a stationary disperser 52. The disperser 52 simultaneously diffracts and focuses a spectrum onto a diode array detector 54. The amount of diffraction of the wavelength components of the transmitted radiation depend on the wavelength values. Thus the wavelength value of the detected radiation at each diode array element is identified based on the location of the respective element. In this type of instrument, the source 42 is usually a deuterium lamp and the disperser 52 is usually a holographic grating superimposed on a concave mirror. The output from the diode array is connected to an analog-to-digital converter via amplifier (both not shown).

Figure 1:
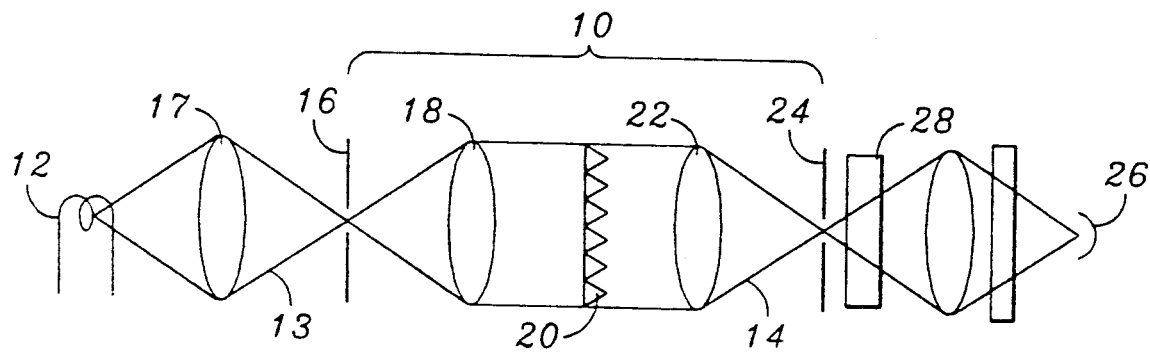
FIG. 1 is a schematic diagram of a conventional scanning spectrophotometer.
Figure 2:
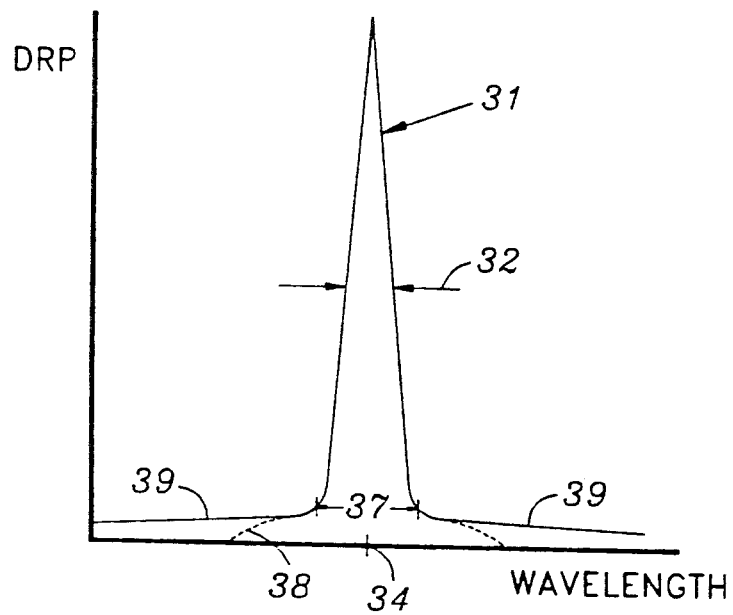
FIG. 2 is a simplified diagram illustrating the spectral characteristic of the radiation detected by the detector in a spectrophotometer.

Each element of the detector array can be thought of as an exit slit (although the array element is always somewhat longer than the equivalent exit slit to allow for errors in system alignment). The spectral distribution of radiant power falling on the detector element will resemble FIG. 2 (assuming unit magnification in the monochromator and detector element width equal to that of the entrance slit). The central wavelengths vary with each detector element in a stepwise manner to cover the designed spectral interval. Thus the signal from each detector element contains a component of primary radiation and a component of stray radiation. Furthermore the signal output of each detector element in the absence of sample absorption will differ depending largely on the source emission spectrum. It is desirable to keep this signal output from each detector element nearly constant in order to keep the dynamic range independent of wavelength. Two methods are used to maintain constant (reference) outputs for each element. One method requires that the length of the sensitive area of the element be made inversely proportional to the DRP falling on the (unmasked) element for the reference measurement. The other method requires that the gain applied to the signal out of the element for the reference measurement be made inversely proportional to the DRP falling on the element. It is not essential that the signals out of each element (in the absence of sample absorption) be constant, but it is essential that the constraints placed on each element must be identical for reference and sample determinations.

Each of the primary radiation and stray radiation components of the signal of each detector element varies depending on whether reference or sample cells are in the beam. Since the spectral character of these two components is different, the sample and reference material will attenuate these two components differently. Thus the determination of sample transmittance at each dial setting (or array detector element) requires knowledge of four DRP values: (1) DRP(P,r), the DRP from primary radiation (P) in the presence of the reference (r); (2) DRP(P,s), the DRP from primary radiation in the presence of the sample (s); (3) DRP(S,r) the DRP from the stray radiation (S) in the presence of the reference; and (4) DRP(S,s) the DRP from stray radiation in the presence of the sample. This is because any one array element can measure only DRP(P+S,r) =DRP(P,r) +DRP(S,r) and DRP(P+S,s) =DRP(P,s) +DRP(S,s), and the desired measurement of sample transmittance is equal to DRP(P,s)/DRP(P,r).

As long as DRP(P,r) is considerably larger than DRP(S,r) and DRP(P,s) is considerably larger than DRP(S,s), one array element can determine accurately a sample transmittance value at the corresponding dial setting. The exact error arising from stray light depends upon the sample transmittance and the dial setting of wavelength. In the presence of any stray light, the error in measured sample transmittance increases as sample transmittance decreases. At the same time the ratio of stray to primary radiation increases as one approaches the extreme wavelength ranges of the instrument. In fact, it may be possible to find a dial setting of wavelength where DRP(P,r) and DRP(P,s) go to zero. At these dial readings (or array element positions) the measured DRP's arise solely from stray light. Recognition of this observation allows one to design a system to compensate for the stray light.

Near the short wavelength limit of any ultraviolet spectrophotometer operated at ordinary atmospheric pressure, the DRP from primary radiation rapidly decreases with decreasing wavelength. This condition arises from the strong absorption of short wavelength radiation by oxygen in the air. If the air path from source to detector is in the vicinity of a foot (approximately 30 cm), the oxygen in the air will absorb essentially all of the radiation of wavelengths shorter than about 185 nm. Most diode array spectrophotometers designed to operate in the ultraviolet range attempt to measure transmittance down to 200 nm in which case the detector array has to extend to the position at which 200 nm radiation will diffract. It is only necessary to extend the array to measure a theoretical 185 nm in response to only stray light in order to compensate for stray light throughout the ultraviolet region. In the prior art, one would not be expected to position an element at a location where no primary radiation can reach the element due to atmospheric absorption. It would have been a waste of expensive array area as stray light compensation using such element was not contemplated in the prior art.

Using the DRP of the stray light measured by the "185 nm" element, the transmittance of a sample at wavelength w then equals $(DRP_w(P+S,s)-DRP_{185}(S,s))/(DRP_w(P+S,r)-DRP_{185}(S,r))$. The subscripts "w" and "185" identify the array elements. It is noted that the gain applied to the array elements may vary from array element — to — array element. It is only necessary that the gain applied to the "185 nm" element be the same as that applied to the "w nm" element when making stray light compensations at wavelength w. Since gain is under software control it may be changed rapidly.

It should be recognized that this method of stray light compensation is of limited accuracy. The intensity of scattered rays is not perfectly uniform across the area of the detector array. The greater the difference (w — 185), the greater the error in stray light compensation. However, the need for stray light compensation is usually greatest near the short wavelength limit of the measurements (close to 185 nm), so this method still has considerable value. Significant errors in stray light compensation only begin for array elements in the higher wavelength range which may be overcoated with a blocking filter. Such blocking filters may be essential to remove second and higher order diffraction attributed to higher order grating dispersion. For example, those array elements designed to detect radiation of wavelengths between 360 and 720 nm will be overcoated with a thin layer of material transparent to these wavelengths but absorbing shorter wavelength radiation. No second order radiation can fall on those array elements designed to detect radiation between 185 and 360 nm because all of such radiation would be absorbed by the oxygen in the air. Furthermore it is usually undesirable to place a blocking filter in the beam when measuring wavelengths shorter than about 360 nm because such filters attenuate the primary radiation in a region where DRP is already lower than optimum.

In one method, blocking filters are inserted into the beam in front of the slit 48. This modifies the spectral range of the instrument hence limits the range of a single "scan". For example, a blocking filter having a cutoff at 360 nm might be inserted. None of the diodes designed to respond to wavelengths shorter than 360 nm can respond to primary radiation. Similarly, none of the elements positioned to respond to radiation longer than 2×360 or 720 nm can be used because they will respond to second order diffracted radiation. The element positioned to respond to 354 nm can be used to measure the stray radiation. It would be desirable to use a tungsten source for this "scan" in the 360 to 720 nm range.

To obtain spectra in the wavelength interval from 720 nm to the upper limit of the detector, one would need to insert a second blocking filter with a cutoff at 720 nm and use the element designed to detect 714 nm radiation to monitor the stray light. A complete ultraviolet to near infrared spectrum will require multiple operations compromising the speed feature of the diode array instrument.

Figure 4:
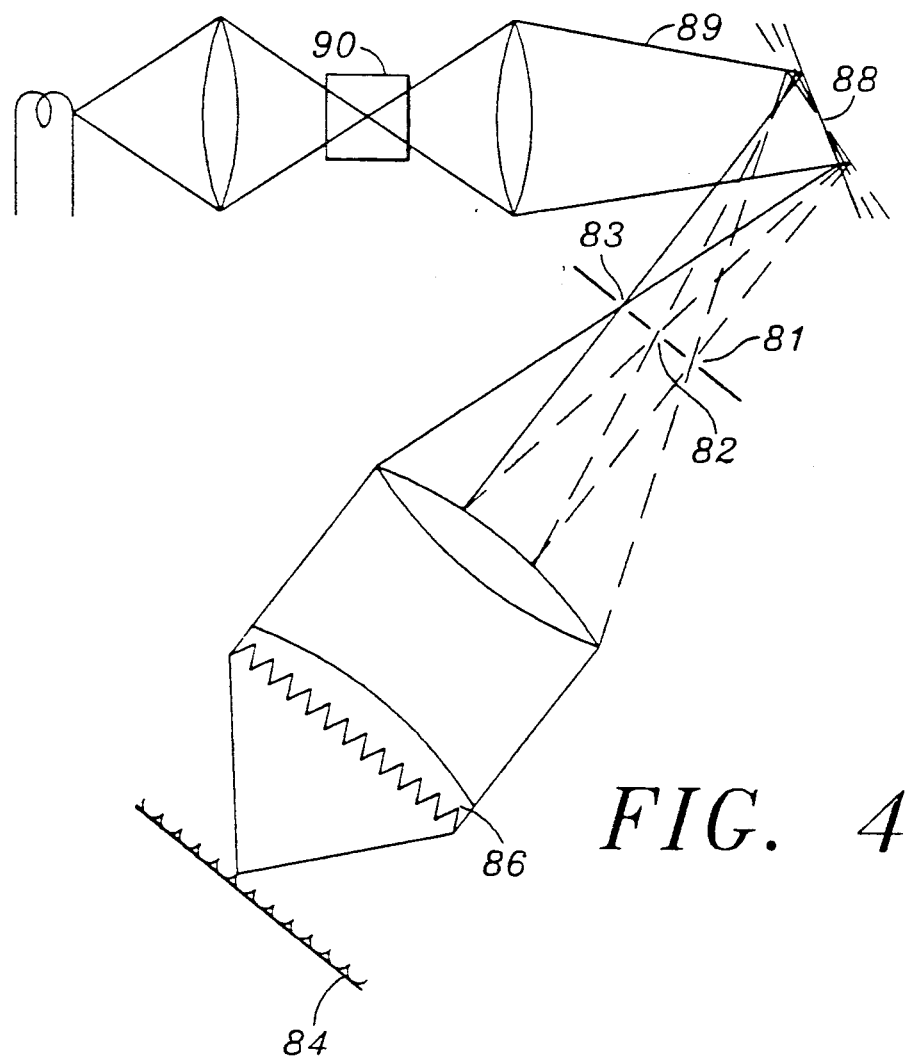
FIG. 4 is a schematic diagram of a modified diode array spectrophotometer.

Referring to FIG. 4 another method is contemplated in an instrument using three slits 80, 81, 82 with a common array 84. The slits 80, 81 and 82 are positioned so that three overlapping segments of the ultraviolet to near infrared region are detected. The dispersion of the grating 86 is roughly three times that required for a single slit instrument if the same array 84 where to be used to cover each of the segments of the spectral interval. Some mechanical means 88 must be employed to direct the source rays 89, after passage through the sample 90, to the three slits 80, 81 and 82 in sequence. Appropriate blocking filters (not shown) can be fixed in position before each of the slits to prevent higher order diffractions. The element for stray radiation detection can be chosen at positions corresponding to the detection of only stray radiation, i.e. below the blocking filter cutoffs. With careful design the same array element can be used to monitor the stray radiation in each wavelength segment. This design optimizes use of the array which at present is still relatively expensive, but introduces additional optical elements (some moving) and extends the time required to obtain a complete ultraviolet to near infrared spectrum.

Figure 5:
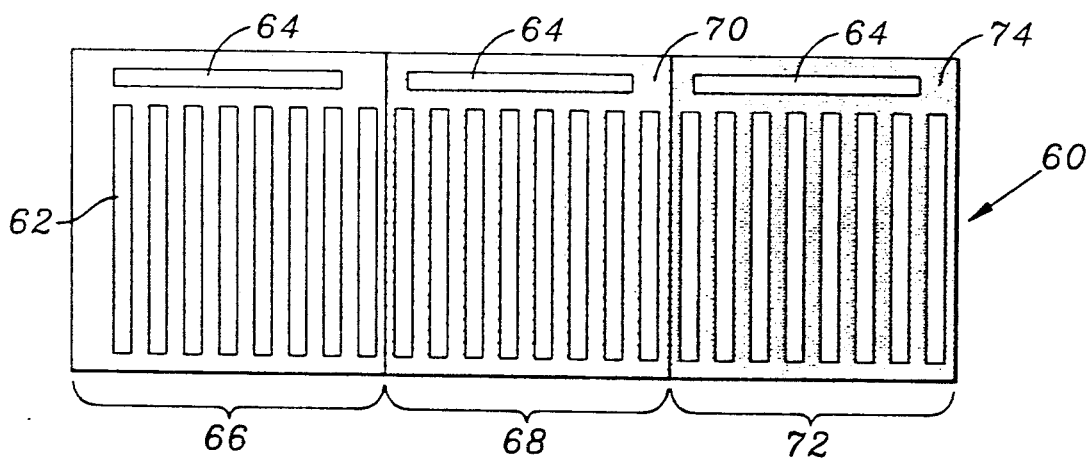
FIG. 5 is a schematic diagram of a diode array detector configuration suitable for use in measuring and compensating for stray radiation.

Another version of the present invention takes advantage of the scatter of stray radiation out of the plane of diffraction (outside the coverage of primary radiation). This method involves the array configuration 60 shown in FIG. 5. The row of vertically oriented array elements 62 continue to be used to detect the primary radiation. However, instead of using an end element (corresponding to 185 nm) of the row of elements to detect stray radiation at a position where the theoretically diffracted rays are totally absorbed by the air in the instrument, special array elements 64 are located as close as possible to the "primary" elements 62, but out of the plane of diffraction. These elements 64 cannot detect the diffracted primary radiation. The stray radiation, which is scattered all over the plane of the array, still reaches elements 64.

The advantage of this arrangement is its utility to compensate for stray radiation over more than one order of diffraction. More than one array element 64 with the orientation out of the plane of diffraction can be used and each one can be overcoated with an appropriate blocking filter.

The left sector 66 of the array 60 is designed to respond to the radiation of wavelength shorter than 360 nm. The middle sector 68 of the array 60 is covered with a thin blocking filter 70 whose cutoff is near 360 nm. The right sector 72 of the array 60 is covered with a high-pass blocking filter 74 whose cutoff is near 720 nm. Since the element 64 used to detect the stray radiation is attenuated in the same (spectral) manner as the elements 62 used to detect primary radiation in the respective sector, this system can compensate for stray radiation over the complete spectral interval of any array spectrophotometer. It is only essential that the primary beam (determined by the height of the entrance slit and system alignment) not fall on the elements 64. Of course the gain applied to element 64 must be the same as that applied to any particular element 62 overcoated with the same blocking filter. Furthermore, if the effective lengths of the elements 62 used to detect primary radiation are abridged (masked) the gain applied to the elements 64 must take this into consideration. Since the masking is fixed the equivalent beam attenuation is constant and taken into consideration in software. It is suggested that lithography techniques be used to "print" the filters directly on the array.

While the invention has been described with respect to the preferred embodiments in accordance therewith, it will be apparent to those skilled in the art that various modifications and improvements may be made without departing from the scope and spirit of the invention. Accordingly, it si to be understood that the invention is not to be limited by the specific illustrated embodiments, but only by the scope of the appended claims.

I claim:

1. A spectroscopic detection device comprising:
   a substrate,
   a primary array of bar shaped radiation detectors for detecting spectroscopic radiation, assembled on said substrate in a linear fashion, the longer sides of said detectors being parallel and proximate to one another, said primary array being positioned so as to be illuminated by direct incidence of spectroscopic radiation, said primary array producing an uncorrected spectroscopic signal;
   a secondary array of bar shaped radiation detectors, assembled on said substrate, for detecting stray radiation impinging on the associated primary array, each detector of said secondary array being oriented in a direction perpendicular to the detectors of the primary array and so that the shorter sides of each secondary array detector are proximate to one another, the detectors of the secondary array being further positioned with respect to the detectors of the primary array so as to each be associated with a plurality of primary array detectors in a non-overlapping manner, said secondary array detectors being located on the substrate in an area not illuminated by direct incidence of spectroscopic radiation, said secondary array detectors producing a signal commensurate with scattered light detected;
   a plurality of filter means superimposed on said primary and secondary arrays and over said substrate for establishing regions of said primary and secondary arrays to be sensitive to predetermined ranges of radiation wavelengths, each of said regions having a plurality of primary array detectors and at least one associated secondary array detector;
   a signal manipulation means for subtracting scattered light signal as detected by secondary array detectors from uncorrected spectroscopic signals detected by the primary array detectors proximate each secondary array detector;
   an output means for providing a corrected spectroscopic signal for further analysis.

2. The device of claim 1 wherein the primary and secondary radiation detectors are photodiodes.

3. The device of claim 1 wherein the range of spectroscopic wavelengths extends from approximately 185 nm to above 720 nm.

4. The device of claim 1 wherein the filter means are filter coatings.

5. The device of claim 4 wherein the number of filter coatings is three, corresponding to three ranges of wavelengths.

6. A multiple element photodetector comprising a parallel array of elongated detector elements, at least one additional elongated detector element arranged generally perpendicular with respect to the detector elements in said parallel array and along one side of the parallel array wherein said at least one additional detector element is associated with a number of said array of detector elements, said at least one additional detector element comprising means for measurement of stray radiation to compensate radiation measurement by said associated array elements.

* * * * *